(12) United States Patent
Venet et al.

(10) Patent No.: US 8,318,753 B2
(45) Date of Patent: Nov. 27, 2012

(54) FARNESYL TRANSFERASE INHIBITING 1,2-ANNELATED QUINOLINE ENANTIOMER

(75) Inventors: Marc Gaston Venet, Le Mesnil-Esnard (FR); Patrick René Angibaud, Fontaine-Bellenger (FR); David William End, Ambler, PA (US)

(73) Assignee: Janssen Pharmaceutica NV, Beerse (BE)

( * ) Notice: Subject to any disclaimer, the term of this patent is extended or adjusted under 35 U.S.C. 154(b) by 1427 days.

(21) Appl. No.: 11/926,741

(22) Filed: Oct. 29, 2007

(65) Prior Publication Data

US 2008/0114009 A1 May 15, 2008

Related U.S. Application Data

(63) Continuation of application No. 11/669,587, filed on Jan. 31, 2007, which is a continuation of application No. 10/312,301, filed as application No. PCT/EP01/06747 on Jun. 13, 2001, now abandoned.

(30) Foreign Application Priority Data

Jun. 22, 2000 (EP) ................................ 00202181

(51) Int. Cl.
- *A01N 43/54* (2006.01)
- *A61K 31/505* (2006.01)
- *C07D 491/00* (2006.01)

(52) U.S. Cl. ........................ 514/267; 544/251
(58) Field of Classification Search .................. 514/267; 544/251
See application file for complete search history.

(56) References Cited

U.S. PATENT DOCUMENTS

| | | | |
|---|---|---|---|
| 4,056,384 A | 11/1977 | Bowie et al. | |
| 4,141,979 A | 2/1979 | Bindra | |
| 6,458,800 B1 | 10/2002 | Angibaud et al. | |
| 6,838,467 B2 | 1/2005 | End | |
| 6,914,066 B2 | 7/2005 | Angibaud et al. | |

FOREIGN PATENT DOCUMENTS

| | | |
|---|---|---|
| WO | WO 97/16443 A1 | 5/1997 |
| WO | WO 97/21701 A1 | 6/1997 |
| WO | WO 97/36876 A1 | 10/1997 |
| WO | WO 98/40383 A1 | 9/1998 |
| WO | WO 98/49157 A1 | 10/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |
| WO | WO 01/62234 A2 | 8/2001 |
| WO | WO 02/24686 A2 | 3/2002 |
| WO | WO 02/24687 A1 | 3/2002 |

OTHER PUBLICATIONS

Zhang, F.L. et. al., "Protein Farnesyltransferase Assays", Current Protocols in Pharmacology, May 2001, pp. 1-6 (http://www.currentprotocols.com/print/53369).*
Pinedo et al.*
McMahon et al.*
Kohl et al., "Selective Inhibition of ras-Dependent Transformation by a Farnesyltransferase Inhibitor", Science, (1993), vol. 260, No. 5116, pp. 1934-1937.
Rak et al., "Mutant ras Oncogenes Upregulate VEGF/VPF Expression: Implications for Induction and Inhibition of Tumor Angiogenesis", Cancer Research, (1995), vol. 55, No. 20, pp. 4575-4580.
Margaritora, S. et al., "Farnesyltransferase Inhibitors Overview of Their Action and Role in solid Malignancy Therapy", Letters in Drug Design & Discovery, (2005), vol. 2, pp. 26-35.
Morgillo, F. and Ho-Young, L., "Development of Farnesyl Transferase Inhibitors as Anticancer Agents: Current Status and Future", Cancer Therapy (2007), vol. 5, pp. 11-18.

* cited by examiner

Primary Examiner — Paul V. Ward
(74) Attorney, Agent, or Firm — Rajiv S. Shah

(57) ABSTRACT

(−)-5-(3-Chlorophenyl)-α-(4-chlorophenyl)-α-(1-methyl-1H-imidazol-5-yl)tetrazolo-[1,5-a]quinazoline-7-methanamine and its pharmaceutically acceptable acid addition salts, and the use of such compounds in medicine especially for the treatment of cancer.

3 Claims, No Drawings

FARNESYL TRANSFERASE INHIBITING 1,2-ANNELATED QUINOLINE ENANTIOMER

CROSS REFERENCE TO RELATED APPLICATIONS

The present application is a continuation of prior application U.S. Ser. No. 11/669,587 filed Jan. 31, 2007, which is a continuation of prior application U.S. Ser. No. 10/312,301, filed Dec. 20, 2002 now abandoned, which application is the national stage of Application No. PCT/EP01/06747, filed Jun. 13, 2001, which application claims priority from EP 00202181.4, filed Jun. 22, 2000, the contents of all of which are incorporated herein by reference in their entirety.

The present invention is concerned with a novel 1,2-annelated quinazoline enantiomer, the preparation thereof, pharmaceutical compositions comprising said novel compound and the use of this compound as a medicine as well as methods of treatment by administering said compound.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl protein transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834-1837, 1993), it has been suggested that farnesyl protein tranferase inhibitors can be very useful against these types of cancer.

In WO 97/16443, WO 97/21701, WO 98/40383 and WO 98/49157, there are described 2-quinolone derivatives which exhibit farnesyl transferase inhibiting activity. Other quinolone compounds having farnesyl transferase inhibiting activity are described in WO 00/12498, 00/12499 and 00/47574. WO 00/39082 describes a class of novel 1,2-annelated quinoline and quinazoline compounds, bearing a nitrogen- or carbon-linked imidazole, which show farnesyl protein transferase inhibiting activity. Among such compounds described in the latter patent specification is (±)-5-(3-chlorophenyl)-α-(4-chlorophenyl)-α-(1-methyl-1H-imidazol-5-yl)tetrazolo[1,5-a]quinazoline-7-methanamine which was obtained in the form of an enantiomeric mixture. We have now separated the mixture and have found that the (−) enantiomer has especially advantageous pharmacological properties compared with the enantiomeric mixture The present invention thus concerns (−)-5-(3-chlorophenyl)-α-(4-chlorophenyl)-α-(1-methyl-1H-imidazol-5-yl)tetrazolo[1,5-a]quinazoline-7-methanamine and its pharmaceutically acceptable acid addition salts.

The above (−) enantiomer is hereinafter referred to as the compound according to the invention.

The compound of the invention is generally present in a substantially pure form, i.e. substantially free of the opposite (+) enantiomer, for example containing less than 5% w/w, preferably less then 2% w/w, and advantageously less than 1% w/w of the latter enantiomer.

The pharmaceutically acceptable acid addition salts as mentioned hereinabove are meant to comprise the therapeutically active non-toxic acid addition salt forms which the compound of the invention is able to form. The latter compound can be converted into its pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compound of the invention is able to form. Examples of such forms are e.g. hydrates, alcoholates and the like.

Whenever used hereinafter, the term "compound of the invention" is meant to include also the pharmaceutically acceptable acid addition salts.

The (−) enantiomer according to the present invention may be prepared by separation of the parent enantiomeric mixture described in the above WO 00/39082. The separation may be effected in conventional manner for example by reaction with a suitable chiral acid such as (+)-6-aminopenicillanic acid, D or L aspartic acid, (1S,3R) or (1R,3S)-camphoric acid, (1S) or (1R)-10-camphorsulfonic acid, carbobenzyloxy-L-proline, cholic acid, dehydrocholic acid, deoxycholic acid, (2S,3S) or (2R,3R) dibenzoyltartaric acid, (2S,3S) or (2R,3R) diacetyltartaric acid, (2S,3S) or (2R,3R)-tartaric acid, (2S,3S) or (2R, 3R) ditoluoyltartaric acid; 2,3:4,6-di-O-isopropylidene-2-keto-L-gulonic acid, (+)-3,4-dihydro-2H-1-benzopyran-2-carboxylic acid, (R) or (S)-4-(2-chlorophenyl)-2-hydroxy-5, 5-dimethyl-1,3,2-dioxaphosphorinane-2-oxide, D-gluconic acid, D or L-glutamic acid, D-isoascorbic acid, (S) or (R)-2-hydroxypropanoic acid, lactobionic acid, D or L-malic acid, (R) or (S)-mandelic acid, L-2-((4-methoxyphenyl)sulfonyl)-amino pentanedioic acid, L-2-((4-methylphenyl)sulfonyl) amino pentanedioic acid, (S)-6-methoxy-α-methyl-2-naphtalene acetic acid, (S)-2-(phenylcarbamoyloxy)-propanoic acid, (−)-3-pinane carboxylic acid, (R) or (S)-2-pyrrolidone-5-carboxylic acid or (R)-thiazolidine-4-carboxylic acid. The resulting salt forms are subsequently separated, for example, by selective or fractional crystallization and the desired enantiomer is liberated therefrom by alkali.

An alternative manner of separating the desired enantiomeric form from the parent mixture involves liquid chromatography using a chiral stationary phase. The pure enantiomeric form may also be derived from the corresponding pure enantiomeric form of the appropriate starting materials, provided that the reaction occurs stereospecifically. The pure enantiomeric form may also be obtained starting from an appropriate racemic starting material provided that the reaction occurs enantiospecifically. The pure enantiomeric form can be prepared by reacting the parent enantiomeric mixture with one enantiomer of some chiral agents such as acids or acid chlorides to obtain diastereoisomeric mixtures, separating it, for example by selective or fractional crystallization or by using liquid chromatography, into pure diastereoisomers. The appropriate diastereoisomer can then be cleaved into the desired enantiomer. The parent enantiomeric mixture may be prepared in accordance with the processes described in the above WO 00/39082 or as described more specifically herein.

The compound of the invention and its pharmaceutically acceptable acid addition salts have valuable pharmacological properties in that they have a farnesyl protein transferase (FPTase) inhibitory effect which is surprisingly potent in comparison with that of the parent enantiomeric mixture. Thus, the latter mixture has a IC50 FPTase inhibitory activity of 1.1 nM whereas the (−) enantiomer has a corresponding activity of 0.7 nM.

This invention provides a method for inhibiting the abnormal growth of cells, including transformed cells, by administering an effective amount of the compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research,* 55, 4575-4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of the compound of the invention to a subject, e.g. a mammal (and more particularly a human) in need of such treatment. In particular, this invention provides a method for inhibiting the growth of tumors expressing an activated ras oncogene by the administration of an effective amount of the compound of the invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compound described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:

a) the sensitisation of tumors to radiotherapy by administering the compound according to the invention before, during or after irradiation of the tumor for treating cancer, for example as described in WO 00/01411;

b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;

c) inhibiting smooth muscle cell proliferation including vascular proliferative disorders, atherosclerosis and restenosis, for example as described in WO 98/55124;

d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;

j) suppressing induction of inducible nitric oxide including nitric oxide or cytokine mediated disorders, septic shock, inhibiting apoptosis and inhibiting nitric oxide cytotoxicity;

k) treating malaria.

Hence, the present invention discloses the compound of the invention for use as a medicine as well as the use of this compound for the manufacture of a medicament for treating one or more of the above mentioned conditions.

For the treatment of the above conditions, the compound of the invention may be advantageously employed in combination with one or more other anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

In view of its useful pharmacological properties, the subject compound may be formulated into various pharmaceutical forms for administration purposes.

To prepare the pharmaceutical compositions of this invention, an effective amount of the compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented above. In general it is contemplated that an effective amount would be from 0.01 mg/kg to 100 mg/kg body weight, and in particular from 0.05 mg/kg to 10 mg/kg body weight. For an adult it is generally preferred to administer a daily dose of 10 to 600 mg, advantageously 50 to 500 mg and especially 100 to 400 mg of active ingredient, doses of 200 or 300 mg being particularly preferred. It may be appropriate to administer the required dose as two, three, four or more sub-doses at appropriate intervals throughout the day. Said sub-doses may be formulated as unit dosage forms, for example, containing 10 to 500 mg, and in particular 50 mg to 300 mg of active ingredient per unit dosage form; dosage units containing 50 mg, 100 mg, 200 mg or 300 mg of active ingredient are especially preferred.

The following examples are provided for purposes of illustration.

EXPERIMENTAL PART

Hereinafter "THF" means tetrahydrofuran, "DIPE" means diisopropylether and "EtOAc" means ethyl acetate.

Example a) Preparation of

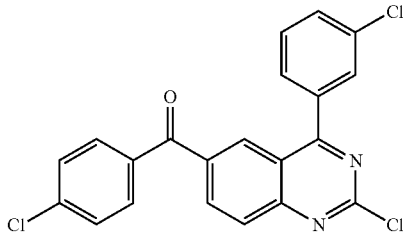

intermediate (2)

A mixture of 6-(4-chlorobenzoyl)-4-(3-chlorophenyl)-2 (1H)-quinazolinone (intermediate 1) (0.0506 mol), prepared as described in WO98/49157, in $POCl_3$ (100 ml) was stirred and refluxed 1 hour. The solvent was evaporated to dryness. The residue was taken up several times in $CH_2Cl_2$. The solvent was evaporated till dryness. The residue was taken up in $CH_2Cl_2$. The mixture was poured out into ice/$NH_4OH$. The organic layer was separated, dried ($MgSO_4$), filtered, and the solvent was evaporated till dryness. The residue (24.2 g) was crystallized from $CH_3CN$. The precipitate was filtered off and dried, yielding: 19.8 g of intermediate (2) (94%), mp. 152° C.

b) Preparation of

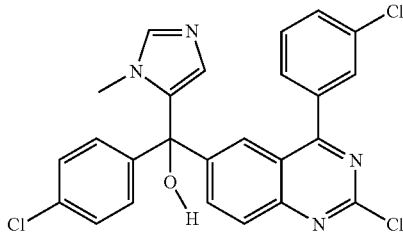

intermediate (3)

A solution of n-butyllithium in hexane (1.6 M) (90 ml) was added dropwise at −70° C. under N2 flow to a mixture of 1-methylimidazole (0.144 mol) in THF (120 ml). The mixture was stirred at −70° C. for 15 minutes. Chlorotriethylsilane (0.148 mol) was added dropwise at −70° C. and the mixture stirred 15 min. at this temperature. A solution of n-butyllithium in hexane (1.6 M) (80 ml) was added dropwise. The mixture was stirred at −70° C. for 15 min. A mixture of intermediate (2) (0.0822 mol) in THF (300 ml) was added dropwise. The mixture was stirred at −70° C. for 1 hour, hydrolysed, extracted with EtOAc and decanted. The organic layer was dried ($MgSO_4$), filtered and the solvent was evaporated. The residue was purified by column chromatography over silica gel. The pure fractions were collected and the solvent was evaporated, yielding 24.9 g (61%) of intermediate (3).

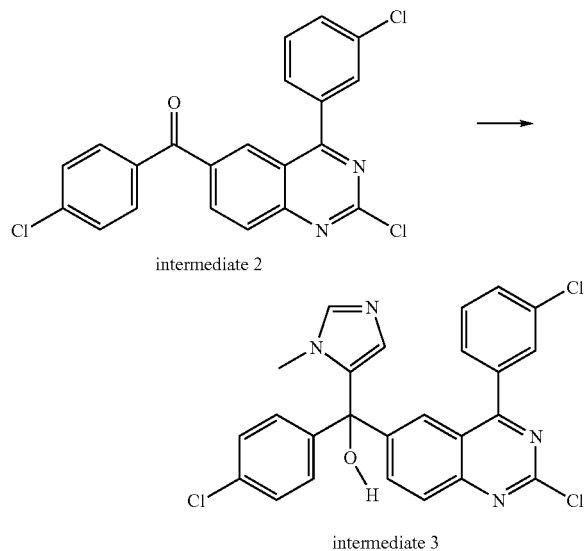

intermediate 2 intermediate 3 c) A mixture of intermediate (3) (0.0061 mol) and sodium azide (0.0079 mol) in N,N-dimethylacetamide (DMA)(20 ml) was stirred at 50° C. for 18 hours. The mixture was cooled to room temperature and poured out into ice water. The precipitate was filtered off, washed with H$_2$O thoroughly and taken up in CH$_2$Cl$_2$. The organic solution was dried, filtered and the solvent was evaporated. The residue was crystallized from CH$_3$CN DIPE. The precipitate was filtered off and dried yielding 2.3 g (75%) of (±)-5-(3-chlorophenyl)-α-(4-chlorophenyl)-α-(1-methyl-1H-imidazol-5-yl)tetrazolo[1,5-a]quinazoline-7-methanol (intermediate 4); mp. 232-233° C.

d) A mixture of intermediate (4) (0.0573 mmol) and sulfonylurea (300 g) was stirred at 160° C. for 5 hours and then cooled. Ice water was added, then methylene chloride and the mixture was filtered over celite. The organic layer was separated, dried (MgSO$_4$), filtered and the solvent was evaporated till dryness. The residue was purified by column chromatography over silica gel. The pure fraction were collected and the solvent was evaporated yielding 7.5 g (26%) of (±)-5-(3-chlorophenyl)-α-(4-chloro-phenyl)-α-(1-methyl-1H-imidazol-5-yl)tetrazolo[1,5-a]quinazoline-7-methanamine (intermediate 5).

e) Intermediate (5) was separated into its enantiomers and purified by column chromatography over Chiralpak AD® (eluent: hexane/EtOH 50/50; 15-35 μm). The pure first (A) fractions were collected and the solvent was evaporated yielding 3.3 g of residue which was crystallized from CH$_3$CN/DIPE. The precipitate was filtered off and dried, yielding 2.55 g of (−)-5-(3-chlorophenyl)-α-(4-chlorophenyl)-α-(1-methyl-1H-imidazol-5-yl)tetrazolo[1,5-a]quinazoline-7-methanamine (compound 1)[α]$_D^{20}$=−7.16°(c=5 mg/ml MeOH); mp.=178-180° C.; 1H-NMR (DMSO, 400 MHz) δ in ppm:

8.73 (d, J=8.6 Hz, 1H), 8.38 (dd, J=8.6 Hz, J=1.5 Hz, 1H); 7.74-7.67 (m, 3H); 7.64 (s, 1H); 7.62-7.56 (m, 2H); 7.40 (d, J=8.6 Hz, 2H); 7.21 (d, J=8.6 Hz, 2H); 5.93 (s, 1H), 3.43 (s, 3H); 3.40 (s, broad, 2H); MS (electrospray, mode pos. OR=50V) m/z: 501-505 (M+H)$^+$; 473-477, 391-395, 83; Anal. (C25H18Cl2N8) C calcd. 59.89 found 59.71, H calcd. 3.62 found 3.52, N calcd. 22.35 found 22.17. This compound contains less than 0.5% w/w of the (+) enantiomer as measured by HPLC (Chiralpak AD® 10 μm eluent Hexane/Ethanol 50/50).

The second (B) fractions were collected and evaporated yielding 3.3 g of residue which was crystallized from CH$_3$CN/DIPE. The precipitate was filtered off and dried yielding 2.6 g of (+)-5-(3-chlorophenyl)-α-(4-chlorophenyl)-α-(1-methyl-1H-imidazol-5-yl)tetrazolo[1,5-a]quinazoline-7-methanamine (compound 2) [α]$_D^{20}$=+5.90° (c=5 mg/ml MeOH). This compound contains 4% w/w of the (−) enantiomer as measured by HPLC (Chiralpak AD® 10 μm eluent Hexane/Ethanol 50/50).

C. Pharmacological Example

Example C.1

In Vitro Assay for Inhibition of Farnesyl Protein Transferase

An in vitro assay for inhibition of farnesyl protein transferase was performed essentially as described in WO 98/40383, pages 33-34.

Example C.2

Ras-Transformed Cell Phenotype Reversion Assay

The ras-transformed cell phenotype reversion assay was performed essentially as described in WO 98/40383, pages 34-36.

Example C.3

Farnesyl Protein Transferase Inhibitor Secondary Tumor Model

The farnesyl protein transferase inhibitor secondary tumor model was used as described in WO 98/40383, page 37.

D. Composition Example

Film-Coated Tablets

Preparation of Tablet Core

A mixture of 100 g of the compound of the invention, 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. (−)-5-(3-chlorophenyl)-α-(4-chlorophenyl)-α-(1-methyl-1H-imidazol-5-yl)tetrazolo[1,5-a]quinazoline-7-methanamine and its pharmaceutically acceptable acid addition salts.

2. A pharmaceutical composition comprising a pharmaceutically acceptable carrier, and as active ingredient a therapeutically effective amount of a compound as claimed in claim 1.

3. A process for preparing a pharmaceutical composition, said composition comprising a therapeutically effective amount of (−)-5-(3-chlorophenyl)-α-(4-chlorophenyl)-α-(1-methyl-1H-imidazol-5-yl)tetrazolo[1,5-a]quinazoline-7-methanamine intimately mixed with a pharmaceutically acceptable carrier.

* * * * *